United States Patent [19]
Rossen et al.

[11] Patent Number: 5,723,615
[45] Date of Patent: Mar. 3, 1998

[54] PROCESS FOR PREPARING 4-TERT-BUTYLOXYCARBONYL-(S)-PIPERAZINE-2-TERT-BUTYLCARBOXAMIDE

[75] Inventors: Kai Rossen, Westfield; Steven A. Weissman, Little Falls; Jess Sager; David Askin, both of Warren; Paul J. Reider, Westfield; Ralph P. Volante, Cranbury, all of N.J.

[73] Assignee: Merck & Co., Inc., Rahway, N.J.

[21] Appl. No.: 665,753

[22] Filed: Jun. 18, 1996

Related U.S. Application Data

[60] Provisional application No. 60/000,588 Jun. 28, 1995.
[51] Int. Cl.[6] .................................................. C07D 241/04
[52] U.S. Cl. .................................................. 544/388; 544/360
[58] Field of Search ................................................ 544/388

[56] References Cited

PUBLICATIONS

Burk. et al., J. Am. Chem. Soc., 1993, 115:10125–10138.
Brunner, et al., Chem. Ber., 1992, 125:2085–2093.
Armstrong, et al., Tetrahedron Letters, 1994, 35(20):3239–3242.
Rossen et al, Tet. Lett. vol. 36, pp. 6419–6422 (Sep. 4, 1995).
Kanozia et al, Chemical Abstracts vol. 125, No. 142774 91996) (Abstract for DE 4446025, Jun. 27, 1996).
Landau et al, Journal of Catalysis 157 pp. 201–208 (1995).

Primary Examiner—Emily Bernhardt
Attorney, Agent, or Firm—Mary A. Appollina; Jack L. Tribble

[57] ABSTRACT

An improved process using chiral hydrogenation is described for the synthesis in high yields of a 4-protected-(S)-piperazine-2-tert-butyl-carboxamide, an intermediate for an HIV protease inhibitor.

11 Claims, No Drawings

PROCESS FOR PREPARING 4-TERT-BUTYLOXYCARBONYL-(S)-PIPERAZINE-2-TERT-BUTYLCARBOXAMIDE

BACKGROUND OF THE INVENTION

This application claims the benefit of U.S. Provisional Application No. 60/000588, filed Jun. 28, 1995.

The present invention is concerned with a novel intermediate and process for synthesizing compounds which inhibit the protease encoded by human immunodeficiency virus (HIV), and in particular certain oligopeptide analogs, such as compound J in the examples below. These compounds are of value in the prevention of infection by HIV, the treatment of infection by HIV and the treatment of the resulting acquired immune deficiency syndrome (AIDS). These compounds are also useful for inhibiting renin and other proteases.

The invention described herein concerns an improved synthesis of 4-tert-butyloxycarbonyl-(S)-piperazine-2-tert-butyl-carboxamide 3 of the structure,

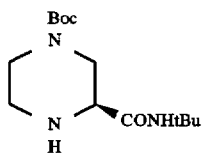

which is an intermediate for the synthesis of the clinically efficacious compound J, of the structure

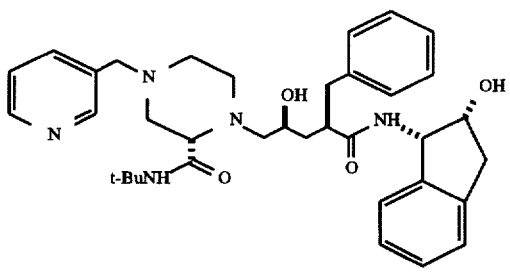

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313, 277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al:, *Science*, 231, 1567 (1986); Pearl, L. H. et al., *Nature*, 329, 351 (1987)]. The end product compounds, including certain oligopeptide analogs that can be made from the novel intermediates and processes of this invention, are inhibitors of HIV protease, and are disclosed in EPO 541,168, which published on May 12, 1993. See, for example, Compound J therein.

Previously, the synthesis of compound J and related compounds was accomplished via a 12-step procedure. This procedure is described in EPO 541,168. In the existing process, 4-tert-butyloxycarbonyl-(S)-piperazine-2-tert-butyl-carboxamide is prepared in a classical resolution of the racemic piperazine-2-tert-butyl-carboxamide. The undesired (R) enantiomer is racemized in a separate step and recycled. This existing process is summarised in Scheme I:

SCHEME I

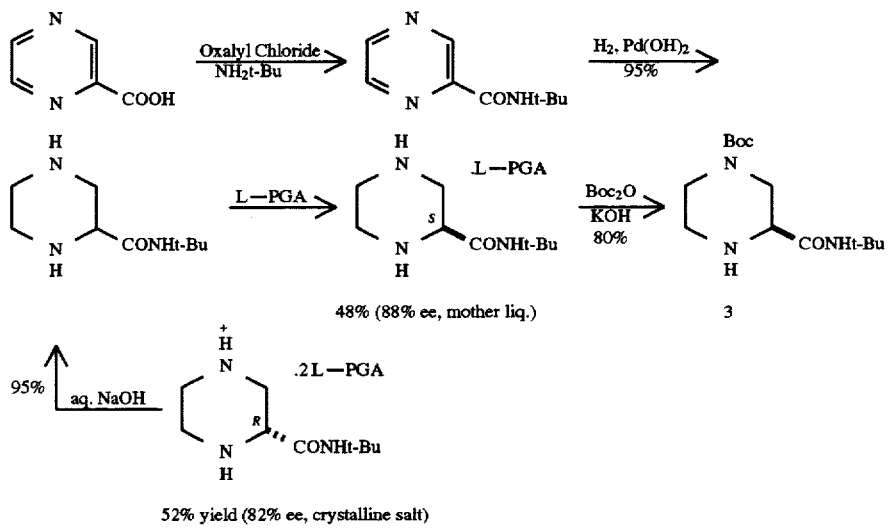

Although this process is high yielding and efficient, it requires a multitude of operations to resolve the racemic amine and then recycle the undesired enantiomer. The process is therefore expensive both in terms of capital investment and manpower. Additionally, the load on the waste stream from the washes and salt breaks is extensive, especially from the resolving agent L-pyroglutamic acid.

Chiral hydrogenation of simple acyclic alpha-(acylamino) acrylic acids and their methyl esters is a known reaction that can occur with high chemical (>95%) and optical yield (>95%) with Rh-chiral bisphosphine catalysts [R. Noyori, Asymmetric Catalysis in Organic Chemistry, John Wiley and Sons, New York, 1994; M. Burk, et al., *J. Am. Chem. Soc.* 1993, 115, 10125]. Unfortunately, chiral hydrogenation of more complex systems is less successful, and both conversion and optical yield drop off dramatically [H. Brenner, et al., *Chem. Ber.* 1992, 125, 2085; J. Armstrong, et al., *Tetrahedron Lett.* 1994, 35, 3239]. Substrates with an olefin as part of a vinylogous urea such as in 1 have not been successfully chirally hydrogenated. It is novel and unexpected to find that the chiral hydrogenation of 1 to 2 described in this invention works in high chemical and optical yield. Also, BINAP derived Rh catalysts are essential for the observed high optical induction. DuPHOS based catalysts that give the best results for simple alpha-(acylamino)acrylic acids give much lower optical induction (<70%).

The present invention is set forth in Scheme II, concerning a novel process for the preparation of the piperazine intermediate 3 for the production of HIV protease inhibitor compound J. The essential step is accomplished by chirally hydrogenating the partially unsaturated tetrahydropyrazine derivative 1 with a Rh-BINAP catalyst to the fully saturated piperazine 2 in 96% yield and 99%ee. Simple hydrogenolytic removal of the Cbz group leads to the intermediate 3. Both the substitution pattern of 1 and choice of catalyst are essential to obtain the high chemical and optical yield.

SCHEME II

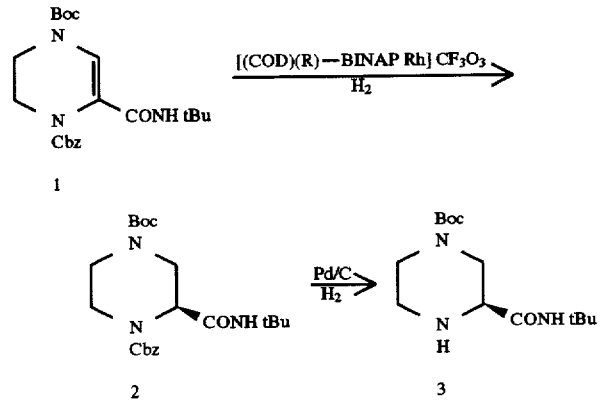

The chiral hydrogenation of the present invention builds up the desired chiral center from a readily accessible starting material in one step in high chemical and optical yield. This is a substantial simplification over the existing procedure, wherein the racemic material is resolved in a classical resolution/racemization of the undesired enantiomer scheme.

BRIEF DESCRIPTION OF THE INVENTION

The present invention provides new methods to effect synthesis in high yields of 4-tert-butyloxycarbonyl-(S)-piperazine-2-tert-butyl-carboxamide, here by chiral hydrogenation. The end product compound is useful as an inhibitor of HIV protease, renin and other proteases.

| TABLE OF ABBREVIATIONS | |
|---|---|
| BINAP | 2,2'bis-(diphenylphosphino)-1,1'-binapthyl |
| Boc | t-Butyl oxycarbonyl |
| Boc-BPPM | (2S,4S)-tert-Butyl 4-(diphenylphosphino)-2-(diphenylphosphinomethyl)-2-pyrrolidine-carboxylate |
| Cbz | Benzyl oxycarbonyl |
| COD | 1,5-cyclooctadiene |
| DIOP | (R,R)-2,3-O-isopropylidene-2,3-dihydroxy-1,4-bis-(diphenylphosphino)-butane |
| DUPHOS | 1,2-Bis((2S,5S)-2,5-diethylphospholano)benzene |
| PROPHOS | 1,2-bis(diphenylphosphino)propane |
| SKEWPHOS | 2,4-bis(diphenylphosphino)pentane |
| TfO | triflate |

DETAILED DESCRIPTION OF THE INVENTION

The present invention provides new methods for making compound J of the structure

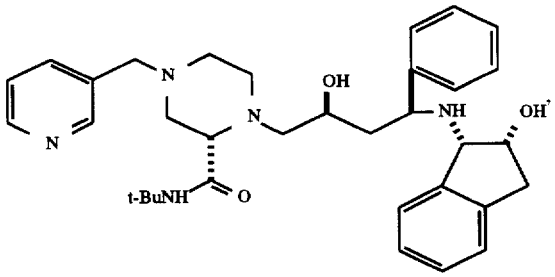

by improvements in the synthesis of an intermediate of the structure

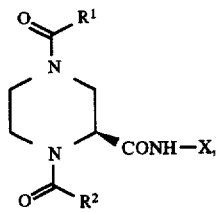

wherein $R^1$ and $R^2$ are independently OX, and X is $C_{1-4}$ alkyl unsubstituted or substituted with aryl or trihalo.

One chiral hydrogenation process in this invention is for the synthesis of a chiral piperazine, of the structure

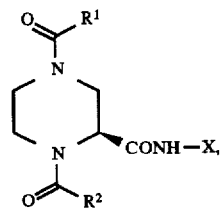

wherein $R^1$ and $R^2$ are independently OX, and X is $C_{1-4}$ alkyl unsubstituted or substituted with aryl or trihalo, and comprises the steps of:

(a) providing a quantity of the compound

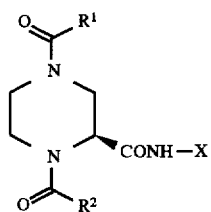

(b) mixing thereto between about 0.1 mole % and about 5 mole % of the catalyst of the structure:
   (diene) Rhodium (chiral bisphosphine) (anionic counterion); or
   (diene) Iridium (chiral bisphosphine) (anionic counterion);

(c) hydrogenating the mixture in solvent in the presence of a hydrogen source, at a temperature between about −10° C. and about 150° C.;

(d) to give the desired chiral piperazine.

Another chiral hydrogenation process of this invention is for the synthesis of a chiral piperazine, of the structure

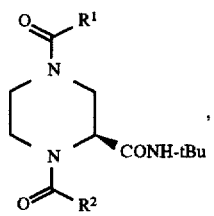

wherein $R^1$ and $R^2$ are independently OX, and X is $C_{1-4}$ alkyl unsubstituted or substituted with aryl or trihalo, and comprises the steps of:

(a) providing a quantity of the compound

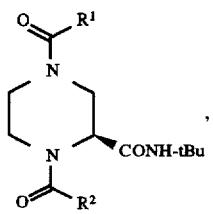

(b) mixing thereto between about 0.1 mole % and about 5 mole % of the catalyst of the structure:
   (diene) Rhodium (chiral bisphosphine) (anionic counterion); or
   (diene) Iridium (chiral bisphosphine) (anionic counterion);

(c) hydrogenating the mixture in solvent in the presence of a hydrogen source, at a temperature between about −10° C. and about 150° C.;

(d) to give the desired chiral piperazine.

One preferred limitation is any of the above processes, wherein
$R^1$ is OtBu;
$R^2$ is OBn.

The diene of the catalyst in the processes of this invention may be selected from the group consisting of 1,5-cyclooctadiene, bicyclo[2.2.1]hepta-2,5-diene, 1,5-hexadiene and two ethylene molecules.

The counterion of the catalyst in the processes of this invention may be selected from the group consisting of perchlorate, tetrafluoroborate, triflate, hexafluorophosphate, and hexafluoroantimonate anion.

The chiral bisphosphine in the processes of this invention may be selected from the group consisting of

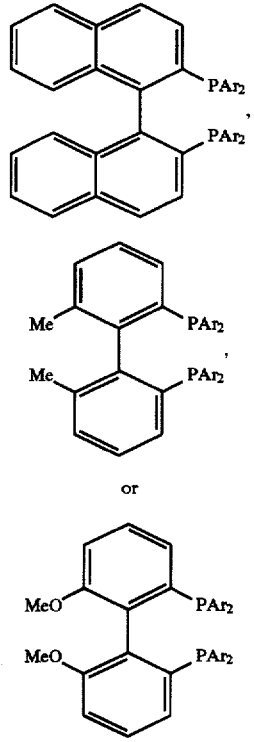

wherein Ar is Ph or tolyl.

The solvent in the processes of the present invention may contain alcohol, said alcohol selected from the group comprising trifluoro ethanol, methanol, ethanol, n-propyl alcohol, isopropyl alcohol, amyl alcohol, butanol, and pentanol.

The source of hydrogen of Step c) may be selected from the group consisting of hydrogen gas, ammonium formate, hydrazine or triethylammonium formate.

In one preferred embodiment, the source of hydrogen is hydrogen gas, and Step c) of the processes given above is carded out under a pressure of between about 0.3 and about 300 atmospheres.

In another preferred embodiment the pressure of hydrogen gas is between about 2 and about 300 atmospheres.

One preferred temperature range for chiral hydrogenation is between about 20° C. and about 100° C.

Another preferred embodiment of the chiral hydrogenation process of this invention is for the synthesis of the chiral piperazine, of the structure

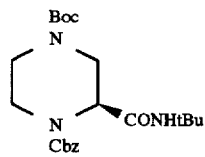

and comprises the steps of:

(a) providing a quantity of the compound

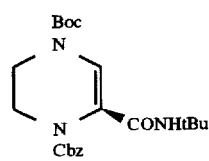

5

(b) mixing thereto between about 0.1 mole % and about 5 mole % of the catalyst of the structure: (R)-BINAP-Rh-(1,5-cyclooctadiene) triflate;

(c) hydrogenating the mixture in alcoholic solvent under hydrogen at a pressure between about 2 and about 300 atmospheres, at a temperature of between about −10° C. and about 150° C.;

(d) to give the desired chiral piperazine.

In the scheme of the present invention, Scheme III,

SCHEME III

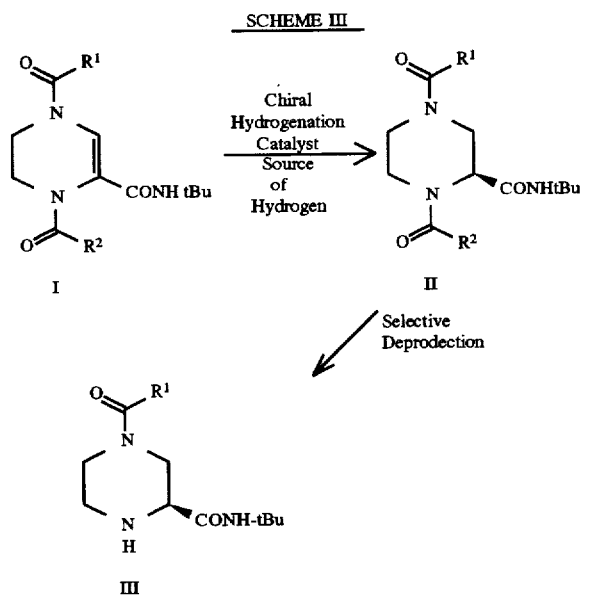

wherein $R^1$ and $R^2$ are independently OX, and X is $C_{1-4}$ alkyl unsubstituted or substituted with aryl or trihalo.

A chiral hydrogenation catalyst of the structure (diene) Rhodium (chiral bisphosphine) (anionic counterion), or (diene) Iridium (chiral bisphosphine) (anionic counterion)

is contacted in solvent with substrate I, then hydrogenated in the presence of a source of hydrogen to give Compound II. Subsequent conventional steps of selective deprotection, such as treatment with palladium on charcoal (when $R^2$=OBn), gives Compound III.

The preferred nitrogen protecting groups of substrate I are Cbz and Boc ($R^1$, $R^2$=OBn, OtBu). The most preferred substrate is 1.

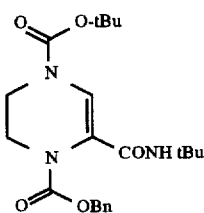

Suitable catalysts for the hydrogenations are Rh-chiral bisphosphine combinations or Ir-chiral bisphosphine combinations, in quantitities ranging from about 0.1 mole % to about 5 mole %. The preferred catalysts are prepared in situ or are isolated, and have the general structure:

(diene) Rhodium (chiral bisphosphine) (anionic counterion), wherein the diene includes but is not limited to 1,5-cyclooctadiene, bicyclo[2.2.1]hepta-2,5-diene, 1,5-hexadiene or 2 ethylene molecules. Preferred chiral bisphosphines include but are not limited to BINAP and its atropisomeric analogues, such as TolBINAP, A or B.

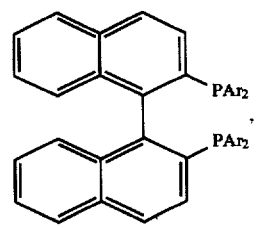

A

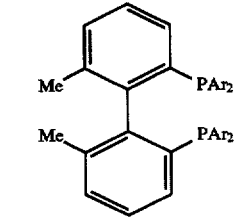

B

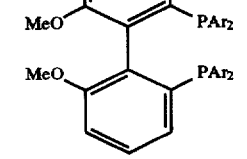

Ar = Ph BINAP
Ar = pCH₃—C₆H₄ TolBINAP

The negatively charged counterion neutralizes the positive charge of the catalytic complex. Preferred anionic counterions include but are not limited to perchlorate, tetrafluoroborate, triflate, hexafluorophosphate ($PF_6^-$), or hexafluoroantimonate ($SbF_6^-$) anion.

Alternative, less preferable catalysts include complexes such as

Rh (chiral bisphosphine) (ROH)₂(anionic counterion), obtained by substituting the diene with a second molecule of an ROH or alcoholic solvent. Another less preferred catalytic complex is generated in situ by reaction of [Rh Cl (diene)₂]₂ with the chiral bisphosphine.

Suitable reaction solvents are an alcohol, an ester, an ether, a halocarbon or an aromatic solvent, or mixtures thereof. Typical alcoholic solvents include but are not limited to methanol, ethanol, trifluoroethanol, n-propyl alcohol, isopropyl alcohol, butanol, or pentanol. Typical ester solvents include but are not limited to ethylacetate and isopropyl acetate. Typical ether solvents include but are not limited to diethylether, tetrahydrofuran. Typical aromatic solvents include but are not limited to benzene and toluene. Typical halogenated solvents include but are not limited to $CH_2Cl_2$, $CHCl_3$.

Preferred solvents for the chiral hydrogenation reaction of the present invention are solvents containing one or more alcohols. Most preferred solvents are alcohols, such as trifluoroethanol, methanol, ethanol, isopropylalcohol, amylalcohol, or mixtures thereof.

A source of hydrogen is needed in the chiral hydrogenation reaction of the present invention. In one embodiment, chiral hydrogenation is performed in the absence of air under a hydrogen atmosphere. Alternatively, standard transfer hydrogenation reagents, such as ammonium formate, hydrazine or triethylammonium formate may be used as a source of hydrogen. The preferred source is hydrogen gas under pressure of between about 0.3 and about 300 atm, most preferably between about 2 and about 300 atm.

The chiral hydrogenation reaction can be performed between about $-10°$ C. and about $150°$ C., but the preferred temperature range is between $20°$ C. and about $100°$ C.

The processes and intermediates of this invention are useful for the preparation of end-product compounds that are useful in the inhibition of HIV protease, the prevention or treatment of infection by the human immunodeficiency virus (HIV), and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

The end product HIV protease inhibitor compound J has the structure

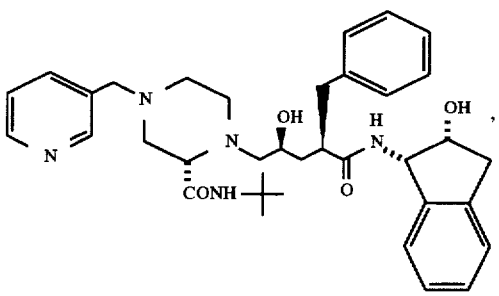

or pharmaceutically acceptable salts or hydrates thereof. Compound J is named N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide;

[1S-[1α[αS*,γR*,δ(R*)],2α]]-N-(2,3-dihydro-2-hydroxy- 1H-inden-1-yl)-2[[(1,1-dimethylethyl)amino]carbonyl]-γ-hydroxy-α-(phenylmethyl)-4-(3-pyridinylmethyl)-1-piperazinepentaneamide; or N-(1(S)-2,3-dihydro-2(R)-hydroxy-1H-indenyl)-4(S)-hydroxy-2(R)-phenylmethyl-5-[4-(3-pyridylmethyl)-2(S)-(t-butylcarbamoyl)-piperazinyl]pentaneamide.

When any variable (e.g., aryl, $R^1$, $R^2$, X, etc.) occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl). As used herein, with exceptions as noted, "aryl" is intended to mean phenyl (Ph) or naphthyl.

HIV protease inhibitor compounds that can be made from the intermediates and processes of the instant invention are disclosed in EPO 541,164. The HIV protease inhibitory compounds may be administered to patients in need of such treatment in pharmaceutical compositions comprising a pharmaceutical carrier and therapeutically-effective amounts of the compound or a pharmaceutically acceptable salt thereof. EPO 541,164 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included in the present invention. Also, combinations of solvents, substituents and/or variables are permissible only if such combinations result in stable compounds.

Representative experimental procedures utilizing the novel process are detailed below. These procedures are exemplary only and are not limitations on the novel process of this invention.

EXAMPLE 1

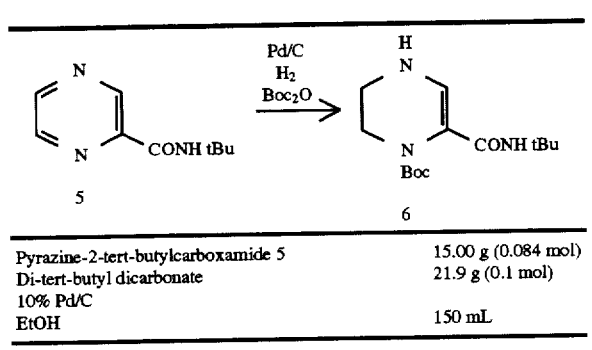

| | |
|---|---|
| Pyrazine-2-tert-butylcarboxamide 5 | 15.00 g (0.084 mol) |
| Di-tert-butyl dicarbonate | 21.9 g (0.1 mol) |
| 10% Pd/C | |
| EtOH | 150 mL |

To a solution of 5 in EtOH was added Pd/C. The reaction was hydrogenated in a Parr shaker at 40° C. and 35° C. for 18 h. The catalyst was filtered off and the filter cake was washed with 100 mL of EtOH. The solvent was switched to EtOAc (ca. 100 mL), and on seeding 6 precipitated as white crystals (17.3 g, 73% yield). $^{13}$C NMR (CDCl$_3$): 165.1, 155.7, 130.0, 129.8, 81.3, 50.5, 41.5, 40.5, 29.2, 28.3.

EXAMPLE 2

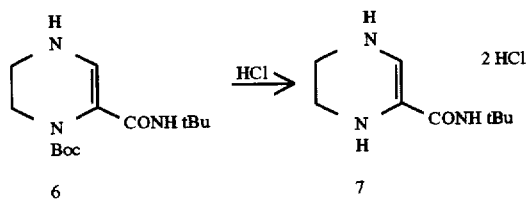

Into a slurry of 6 (18.58 g, 0.066 Mol) in 200 mL EtOAc was bubbled an excess of HCl gas at 10°–15° C. The resulting slurry was aged overnight at 20° C. and filtered. The filtrate was washed with EtOAc and hexane and dried in a N$_2$ stream to give 7·2 HCl (16.42 g, 98%).

EXAMPLE 3

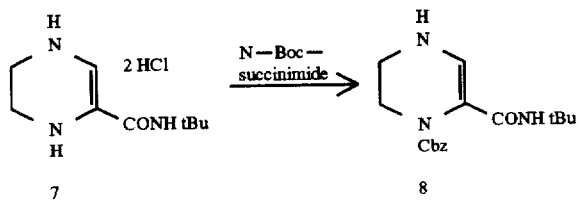

A slurry of 7·2 HCl (12.09 g; 0.047 Mol) in 160 mL EtOAc was degassed in a N$_2$ stream and cooled to 5° C. Et$_3$N (16.5 mL, 0.12 Mol) and N-(benzyloxycarbonyloxy)succinimide (12.35 g, 0.05 Mol) were added and the reaction mixture was stirred at 22° C. overnight. The reaction mixture was washed with H$_2$O, 5% citric acid, 5% NaHCO$_3$ and brine. After drying (MgSO$_4$), the organic phase was filtered through a plug of SiO$_2$ and evaporated. Crystallization from EtOAc/cyclohexane 10/90 gave 8 (9.39 g, 63% yield). Anal. Calcd for C$_{17}$H$_{23}$N$_3$O$_3$: C, 64.33; H, 7.30; N, 13.24. Found: C, 64.23; H, 7.31; N, 13.17. mp 161°–162° C.

EXAMPLE 4

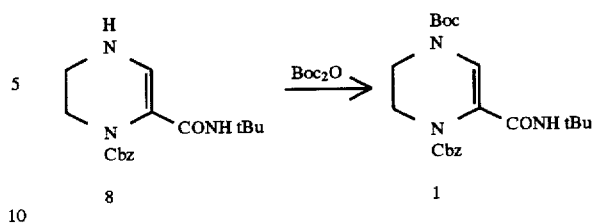

To a slurry of 8 (18.59 g, 0.059 Mol) in 120 mL isopropyl acetate was added Boc$_2$O (20 mL, 0.12 Mol) and diisopropylethylamine (1 mL). On heating to reflux the reaction mixture turned homogeneous and was refluxed for 18 h. The reaction mixture was evaporated and chromatographed (SiO$_2$, EtOAc/hexane 50/50) to give 1 as an oil (24.5 g, 100%). Crystallization from cyclohexane/isopropyl acetate 10/1 gave 1 as a white solid. Anal. Calcd for C$_{22}$H$_{31}$N$_3$O$_5$: C, 63.29; H, 7.48; N, 10.06. Found: C, 63.30; H, 7.40; N, 9.94. mp. 99°–100° C.

EXAMPLE 5

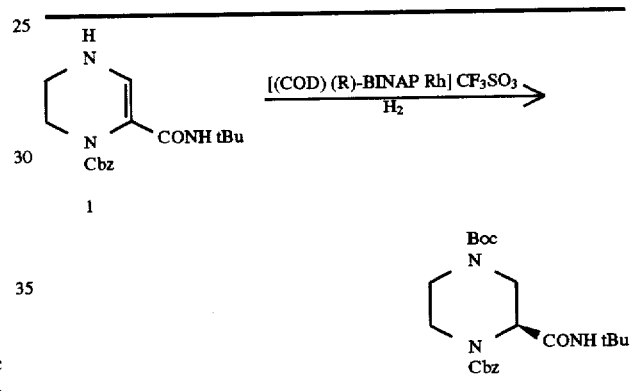

A. First Protocol

| | |
|---|---|
| Boc-Cbz-Tetrahydropyrazine-tert-butyl-carboximide 1 | 0.204 g (0.49 mmol) |
| [(R)-BINAP Rh (1,5-cyclooctadiene)] triflate | 14 mg (3 mol %) |
| Trifluoroethanol | 10 mL |

A solution of 1 in CF$_3$CH$_2$OH in a high pressure hydrogenation tube was degassed for 15 min. in a N$_2$ stream. The catalyst was added under N$_2$ and the clear solution in the high pressure tube was put into a hydrogenation rocker. The vessel was purged with 3 H$_2$/vacuum cycles and then put under 1000 psi of H$_2$ and heated to 40° C. for 72 h. TLC (EtOAC/Hex 50/50) indicated complete conversion. The solution was evaporated and purified by SiO$_2$ chromatography to give 178 mg (87% yield) of 2 as an oil that crystallised on standing. Chiral HPLC (Chiracell AD, IPA/Hexane 15/85, 0.6 mL/min, 225 nm detection, RT (S) isomer 10.7 min, (R) isomer 9.0 min) showed that the product was 95% ee for the (S) isomer. [alpha] 589=–7.6°. $^1$H NMR (CDCl$_3$, 22° C.): 7.3 (5H), 5.9 (1H), 5.2 (dd, 2H), 4.5 (2H), 3.9 (2H), 2.9–3.3 (3H), 1.5 (9H), 1.3 (9H).

B. Second Protocol

A solution of 1 (0.433 g, 1.04 mmol) in 10 mL of MeOH in a high pressure hydrogenation tube was degassed with N$_2$ for 10 min. The catalyst ([(R)-BINAP (COD) Rh]TfO, 21 mg, 2 mol%) was added. After 3 vacuum/H$_2$ flushes the system was pressurized to 70 bar of $H_2$ and heated to 40° C. After 18 h the solution was evaporated and chromatographed ($SiO_2$, EtOAc/hexane 50/50) to give 417 mg (96%) of a white solid of 99% ee. Anal. Calcd for $C_{22}H_{33}N_3O_5$: C, 62.99; H, 7.93; N, 10.02. Found: C, 63.04; H, 7.86; N, 10.05. mp 136°–137° C.

EXAMPLE 6

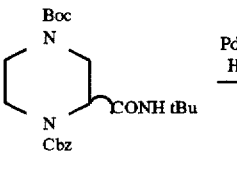

| | |
|---|---|
| (S)-Cbz-Boc-Piperazine-2-tert-butyl-carboxamide 2 | 1.055 g (2.52 mmol) |
| Pearlman's catalyst | 0.157 g |
| MeOH | 16 mL |

To a solution of 2 in MeOH was added Pearlman's catalyst. The solution was hydrogenated at 40 psi and 22° C. TLC (EtOAc/hex 50/50) indicated completion of the reaction. The catalyst was removed by filtration and the filtrate was evaporated. Cyclohexane (5 mL) was added and the oil was dissolved by heating. On cooling 3 precipitated and was filtered to give after drying 0.7 g (99%) of 3 as a white powder. [alpha]589=22° (c=0.2, MeOH), m.p. 107° C.; $^{13}C$ NMR ($CDCl_3$) 170.1, 154.5, 79.8, 58.7, 50.6, 46.6, 43.6, 43.4, 28.6, 28.3.

EXAMPLE 7

A. Conversion of Indene Oxide to Cis-1-Amino-2-Indanol

| Materials | Mol. Wt. | Grams or ml | Millimoles |
|---|---|---|---|
| Indene oxide | 132 | 1 ml | 8.33 |
| Acetonitrile | 41 | 10 ml | 244 |
| Water | 18 | 2.15 ml | 119.4 |
| Conc. $H_2SO_4$ | 98 | 0.92 ml | 16.6 |
| 5N KOH | 57 | 3.0 ml | 15 |
| Dowex 50 × 4 (H+) | 1.9 meq/ml | 15 ml wet resin | 28.5 meq |
| Methanol | 17 | 50 ml | 50 |

To one ml of indene oxide (8.33 mmoles) dissolved in 10 ml acetonitrile was added 0.15 ml water (8.33 mmoles). The mixture was cooled to 0°–5° in an ice bath. Concentrated sulfuric acid was added dropwise while maintaining the batch temperature below 10°. When all the acid was added and the temperature was allowed to rise to 20°–25°. The clear solution was aged for 30 minutes.

To this mixture was added 2 ml of water and the solution heated for 30 minutes. When the methyl oxazoline was completely converted to cis amino indanol the reaction mixture was cooled to room temperature.

A solution of 5N KOH (3 ml, 15 mmoles) was added. This is 90% of theory for the sulfuric acid. The solution remained acid to litmus. If the pH rises above, 2 re-acylation occurs and the yield of amino indanol is reduced. The white solid ($K_2SO_4$) was removed by filtration.

Dowex resin 15 ml (wet with acetonitrile) was added with stirring. The stirred resin was aged for 15 minutes and sampled for LC (dilx 50). When the LC peak for amino indanol disappeared, the resin was collected by filtration, washed with acetonitrile and then with methanol.

The wet resin was treated with a solution of 50 ml 1N $NH_3$ in methanol and the slurry stirred at room temperature for 30 minutes. The resin was again collected by filtration and the methanol/$NH_3$ saved. Another charge of 1N $NH_3$/MeOH (20 ml) was added and the resin reslurried. After removal of the resin the methanol/$NH_3$ solutions of the amino indanol were combined and concentrated to remove the $NH_3$. Analysis of the final MeOH solution shows 1.0 g (81% yield) cis-1-amino-2-indanol ready for the tartaric acid resolving agent.

B. Preparation of racemic indene oxide

Indene (95%, 122 mL) was dissolved in methanol (812 mL) and acetonitrile (348 mL), then filtered. The filtrate was diluted with 0.05M sodium dibasic phosphate (116 mL), then adjusted to pH 10.5 with 1M aqueous sodium hydroxide. Aqueous hydrogen peroxide (35%, 105 mL) was diluted with water (53 mL) and added over 3 h, while maintaining the temperature at 25° C. and the internal pH at 10.5 with 1M aqueous sodium hydroxide (120 mL total).

After 6 h, 1M aqueous sodium metabisulfite was added (26 mL), while maintaining the pH above 8.3 by addition of 1M aqueous NaOH (39 mL). Water (700 mL) was added and the mixture extracted with methylene chloride (580 mL and 300 mL). The combined organic extracts containing indene oxide (117 g) were concentrated to a volume of 600 mL.

C. Preparation of (1S, 2R)-indene oxide

The substrate, (1S, 2R)-indene oxide is prepared according to the method described by D. J. O'Donnell, et al., *J. Organic Chemistry*, 43, 4540 (1978), herein incorporated by reference for these purposes.

D. Preparation, of cis-1-amino-2-indanol

Indene oxide (117 g) diluted to a total volume of 600 mL in methylene chloride was diluted with acetonitrile (600 mL) and cooled to −20° C. Methanesulfonic acid (114 mL) was then added. The mixture was warmed to 25° C. and aged for 2 h. Water (600 mL) was added and the mixture heated at 45° C. for 5 h. The organic phase was separated and the aqueous phase further heated at reflux for 4 h with concentration to approximately 200 g/L. The solution was adjusted to pH 12.5 with 50% aqueous sodium hydroxide, and then cooled to 5° C. and filtered, dried in vacuo, to provide cis 1-amino-2-indanol.

E. Preparation of 1S-amino-2R-indanol (1S, 2R)-indene oxide (85% ee.) (250 g, 0.185 mole) was dissolved in chlorobenzene (300 mL) and heptanes (1200 mL) and slowly added to a solution of methanesulfonic acid (250 mL, 0.375 mole) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C. for 2–3 h then cooled to room temperature. Chlorobenzene (1000 mL) was added, the mixture stirred, the organic phase separated. The remaining aqueous phase containing 1S-amino, 2R-indanol (85% ee, 165 g, 60%) was adjusted to pH 12 with 50% aqueous sodium hydroxide and the product collected by filtration and dried in vacuo at 40° C. to yield 1S-amino, 2R-indanol (85% ee, 160 g).

F. Preparation of 1S-amino-2R-indanol (1S, 2R)-indene oxide (85% ee.) (250 g, 0.185 mole) was dissolved in chlorobenzene (300 mL) and heptanes (1200 mL) and slowly added to a solution of fuming sulfuric acid (21% $SO_3$, 184 mL) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C..for 2–3 h, then cooled to room temperature. Chlorobenzene (1000 mL) was added, the mixture stirred, the organic phase separated. The remaining aqueous phase containing 1S-amino, 2R-indanol (85% ee, 205 g, 74%) was diluted with an equal volume of acetonitrile. The pH was adjusted to 12.5 with 50% aqueous sodium hydroxide and the organic phase separated. The remaining aqueous phase was extracted with additional acetonitrile. The combined acetonitrile extracts were concentrated in vacuo to provide 1S-amino, 2R-indanol (85% ee, 205 g).

Alternatively, the remaining aqueous phase containing 1S-amino-2R-indanol (85% ee, 205 g, 74%) was diluted with an equal volume of butanol and the pH was adjusted to 12.5 with 50% aqueous sodium hydroxide and the organic phase separated. The organic phase was washed with chlorobenzene. L-tartaric acid was added and water was removed by distillation to crystallize the tartaric acid salt of the amino-indanol.

G. Use of benzonitrile

Indene oxide (5 g) was dissolved in benzonitrile (50 mL) at 25° C. and sulfuric acid (98%, 2.25 mL) was added. The mixture was diluted with 5M aqueous sodium hydroxide solution (50 mL) and extracted with methylene chloride. The organic extracts were concentrated in vacuo to give 5.03 g of oxazoline.

H. Resolution of cis-1-Amino-2-indanol

Cis-1-Amino-2-indanol (100 g) was dissolved in methanol (1500 mL) and a solution of L-tartaric acid (110 g) in methanol (1500 mL) was added. The mixture was heated to 60° C. and cooled to 20° C., filtered and dried in vacuo to give 1S-amino, 2R-indanol L-tartaric acid salt as a methanol solvate (88 g).

I. Preparation of 1S-Amino--2R-indanol

1S-Amino, 2R-indanol L-tartaric acid salt methanol solvate (88 g) was dissolved in water (180 mL) and heated to 55°–60° C. The solution was clarified by filtration and the pH adjusted to 12.5 with 50% aqueous sodium hydroxide. The mixture was cooled to 0°–5° C. over 2 h, then aged at that temperature for 1 h, filtered, washed with cold water and dried in vacuo at 40° C. to yield 1S-amino, 2R-indanol (100% ee, 99% pure, 37 g).

J. Conversion of 1,2indanol to cis-1-amino-2-indanol

| Materials | Mol Wt | Grams or ml | Millimoles |
| --- | --- | --- | --- |
| 1,2 indane diol | 150 | 300 mg | 2 |
| acetonitrile | 41 | 2.5 ml | 47.3 |
| water | 18 | 0.04 ml | 2 |
| sulfuric acid | 98 | 0.22 ml | 4 |

| Materials | Mol Wt | Grams or ml | Millimoles |
| --- | --- | --- | --- |
| 5 N KOH | 57 | 1.6 ml | 8.0 |
| Dowex 50 × 4 (H+) | | 10 ml | |
| methanol (1 m NH$_3$) | | 30 ml | |

To 300 mg indane diol dissolved in 3 ml of acetonitrile containing 0.04 ml water was added dropwise at 0°–10° C. a volume of 0.22 ml of concentrated H$_2$SO$_4$. After the addition was complete the ice bath was removed and the batch warmed to room temperature. After a 30 minute age the clear solution was sampled for Ic assay (dilx 500). When all the glycol was consumed, the solution was treated further with water and heated to reflux on a steam bath to hydrolyze the oxazoline.

When Ic analysis showed hydrolysis complete, 1.6 ml 5N KOH was added to neutralize the sulfuric acid. Potassium sulfate was filtered from the solution.

The filtrate was assayed for cis amino indanol and contained 196 mg (66% of theory, which is also 75% corrected for unreacted starting material). The solution was passed over 10 ml of Dowex 50×4 (H+). The column spents were checked for product. All the amino indanol was adsorbed. After washing the resin with methanol, the product was eluted with a solution 1M in NH$_3$ (dry). The ammoniacal methanol was concentrated to remove the NH$_3$ and the final solution of amino-indanol ready for resolution was assayed. (175 mg, or 59% of theory when uncorrected for unreacted glycol).

K. Preparation of Indanol Reactants

Compounds (±)-trans-2-bromo-1-indanol were prepared by methods of S. M. Sutter et al., *J. Am. Chem. Soc.*, 62, 3473 (1940); and D. R. Dalton et al., *J. C. S. Chem. Commun.*, 591 (1966). Compounds (+)-trans-2-bromo-1-indanol and cis- and trans-1,2-indandiols were prepared by the methods of M. Imuta et al., *J. Org. Chem.*, 43, 4540 (1978).

L. Preparation of cis-1-amino-2-indanol from trans-2-bromo-1-indanol

Trans-2-bromo-1-indanol (10 g, 46.9 mmole diluted in 100 mL of acetonitrile containing 0.8 mL water) was cooled to –5° C. and concentrated sulfuric acid (5.2 mL) was added. The mixture was aged for 1 h, then 5M aqueous potassium hydroxide was added to adjust the pH to 11. The reaction mixture was filtered, removing the potassium sulfate salts. The aqueous acetonitrile filtrate was adjusted to pH less than 2 with sulfuric acid and heated to 80°–100° C., removing acetonitrile by distillation to provide an aqueous solution of cis-1-amino-indanol. The solution was concentrated to a volume of 20 mL, then adjusted to pH 12.5 with potassium

17 hydroxide. The product crystallizes, was filtered and dried in vacuo to provide cis-1-amino-2-indanol (4.25 g).

M. Preparation of cis-1S-amino-2R-indanol from cis-(1S, 2R)-indandiol

Cis-(1S,2R)-indandiol (1 g) was dissolved in acetonitrile (10 mL), cooled to 0° C. and concentrated sulfuric acid (1.0 mL) was added. The mixture was aged for 40 minutes with warming to 20° C. Water (0.8 mL) was added and the mixture was heated to reflux. Aqueous 5M potassium hydroxide (1.6 mL) was added to adjust the pH to more than 11 and the resulting solid (potassium sulfate) removed by filtration to provide an aqueous solution of the cis-1S-amino-2R-indanol (0.79 g, 66% yield).

N. Preparation of cis-1-amino-2-indanol from trans-1,2-indandiol

Trans-1,2-indandiol (1.5 g) was dissolved in acetonitrile (25 mL) cooled to 0° C., and concentrated sulfuric acid (1.1 mL) was added. The mixture was gradually warmed to 20° C. and aged to 3 hours. Water (2 mL) was added and the mixture heated to reflux. Concentrated aqueous sodium hydroxide was added to adjust the pH to 12. The resulting solid was removed by filtration to provide an aqueous acetonitrile solution of cis-1-amino-2-indanol (1.02 g, 63% yield).

O. Preparation of cis-1-amino-2-indanol from cis-1,2-indandiol

Cis-1,2-indandiol (1.0 g) was dissolved in acetonitrile (20 mL), cooled to −40° C., and fuming sulfuric acid (21% SO$_3$, 0.8 mL) was added. The mixture was aged for 1 hour with gradual warming to 0° C. Water was added and the mixture heated to 80° C. for 1 hour to provide an aqueous solution of cis-1-amino-2-indanol.

18

EXAMPLE 8

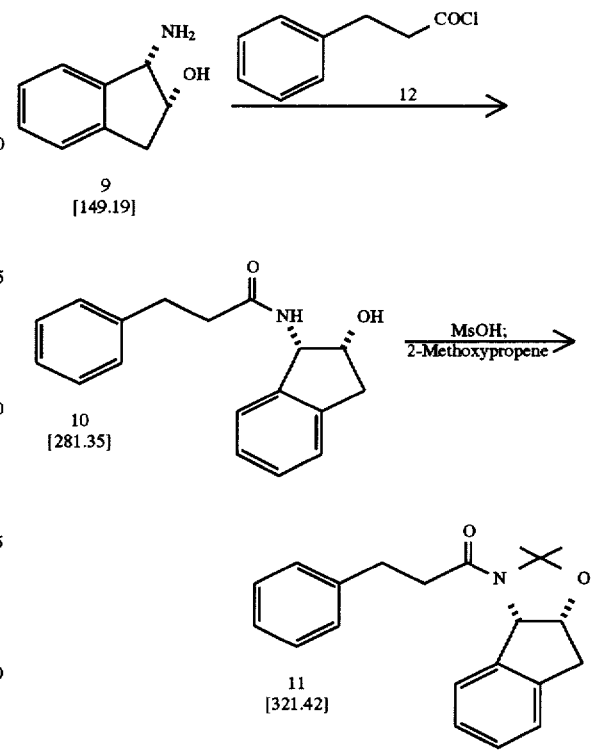

Preparation of Acetonide 11

| | | |
|---|---|---|
| (−)-cis-1-aminoindan-2-ol (9) (99.7 wgt. %, 99.9 area %, >99.5% ee) | 900 g | 6.02 mol |
| sodium carbonate monohydrate | 760 g | 6.13 mol |
| diethoxymethane (DEM) | 56.3 L | |
| 3-phenylpropionyl chloride (12) | 1.05 kg | 6.23 mol |
| methanesulfonic acid (MSA) | 18.6 g | 0.19 mol |
| 2-methoxypropene (95% by GC) | 1.28 L | 13.3 mol |
| 5% aqueous NaHCO$_3$ | 10.8 L | |
| water | 26.2 L | |

A slurry mixture consisting of (−)-cis-1-aminoindan-2-ol (9.900 g, 6.02 mol) in 40 L of DEM and aqueous sodium carbonate solution (760 g, 6.13 mol, of $Na_2CO_3 \cdot H_2O$ in 6.4 L of water) in a 100 L reactor with four inlets, equipped with a thermocouple probe, mechanical stirrer, and a nitrogen inlet adapter and bubbler, was heated to 46°–47° C. and aged for 15 minutes. The reaction mixture was heated to 46°–47° C. and aged for 15 minutes to insure dissolution of the solids. The aqueous phase had a pH of 11.5. Neat 3-phenylpropionyl chloride 12 (1.05 kg, 6.23 mol) was added over 2 h between 47° C. to 59° C. The internal temperature increased from 47° C. to 59° C. during the addition of 12; the hydroxyamide 10 crystallized out of solution during the acid chloride addition. After the addition was complete, the reaction mixture was aged at 59° C. for 0.5 h and then warmed to 72° C. to insure dissolution of the solids. The temperature was increased to 72° C. to dissolve the hydroxyamide so that a homogeneous sample can be obtained for HPLC assay and to simplify the phase cuts. Progress of the reaction was monitored by HPLC analysis: 60:40 Acetonitrile/5.0 mM of each $KH_2PO_4$ and $K_2HPO_4$. Approximate retention times:

| retention time (min.) | identity |
|---|---|
| 4.1 | hydroxy amide 10 |
| 6.3 | cis-aminoindanol 9 |
| 12.5 | ester amide by product |

After complete acid chloride addition and 0.5 h age at 72° C., the HPLC assay of the reaction mixture showed ~0.6 area % of 9, ~0.2 area % of ester amide by product and 98.7 area % of hydroxyamide. The hydroxy amide 10 was not efficiently rejected in the isolation of acetonide 11. The aqueous phase was separated and the organic phase was washed twice with 4.5 L of water. The washed organic phase was concentrated and dried via atmospheric azeotropic distillation. The initial volume of ~40 L was concentrated to 27 L. A total of 16 L of fresh DEM was charged to the still and the batch was concentrated at 88° C. to 89° C. to 40 L.

The dried DEM slurry of hydroxyamide 10 was treated with 1.28 L of 2-methoxypropene followed by 18.6 g of MSA at 30° C. The addition of MSA in absence of 2-methoxypropene resulted in the formation of an amine ester. This impurity reconverts to hydroxyamide 10 during the basic work up at the end of the acetonide formation. The pH of 1.0 mL sample diluted with 1.0 mL water was found to be 2.8–3.0. The resulting mixture was aged at 39° C. to 40° C. for 3 h. The acetonide formation was monitored by HPLC analysis using the same conditions as described above in this example. Approximate retention times:

| retention time (min.) | identity |
|---|---|
| 4.1 | hydroxy amide 10 |
| 6.9 | methylene ketal impurity |
| 9.0 | acetonide 11 |
| 12.5 | ester amide by product |

The mixture was aged at 38°–40° C. until 10 is ≦0.4 A%. A typical HPLC area % profile is as follows: 0.4 area % of hydroxyamide 10, 96.9 area % of acetonide 11, 0.2 area % of ester amide by product, 1.1 area % of methylene ketal impurity. The reaction mixture was cooled to 24° C. and quenched with 10.8 L of 5% aqueous sodium bicarbonate solution. The aqueous phase was separated and the organic phase was washed twice with 10.8 L of water. The pH of the water wash was 7.6. If the pH was too low, the acetonide group could be hydrolyzed back to give the hydroxyamide 10. The washed organic phase (34.2 L) was concentrated via atmospheric distillation at 78° C. to 80° C. to final volume of 3.5 L. The acetonide concentration was made ~525 g/L to minimize isolation losses. The hot DEM solution of 11 was allowed to cool to 57° C., seeded with 0.5 g of 11 and further cooled to 0° C. and aged for 0.5 h. The batch started to crystallize out of solution between 53° C. to 55° C. The product was isolated by filtration and the wet cake was washed with cold (0° C.) DEM (300 mL). The washed cake was dried under vacuum (26" of Hg) at 30° C. to afford 1.74 kg of acetonide 11 (90%, >99.5 area % by HPLC).

EXAMPLE 9

Preparation of Acetonide 11 from (9.tartaric acid) salt

| | | |
|---|---|---|
| (−)-cis-1-aminoindan-2-ol tartrate salt methanol solvate (44.3 wt. % of free base 9) | 100 g | 297 mmol |
| sodium carbonate monohydrate | 63.76 g | 514 mmol |
| diethoxymethane (DEM) | 2.83 L | |
| 3-phenylpropionyl chloride (12) | 52.7 g | 312 mol |
| methanesulfonic acid (MSA) | 0.95 g | 9.86 mmol |
| 2-methoxypropene (95% by GC) | 63 mL | 658 mmol |
| 5% aqueous $NaHCO_3$ | 520 mL | |
| water | 1.32 L | |

A slurry mixture consisting of (−) 9.tartrate salt methanol solvate (100 g, 44.3 g of free base, 297 mmol) in 2.0 L of (DEM) and aqueous sodium carbonate solution (63.8 g, 514 mmol, of $Na_2CO_3 \cdot H_2O$ in 316 mL of water) in a 5.0 L reactor with four inlets, equipped with a thermocouple probe, mechanical stirrer, and a nitrogen inlet adapter and bubbler, was heated to 50° C. Heating the reaction mixture to 60° C. did not dissolve all the solids. Neat 3-phenylpropionyl chloride 12 (52.7 g, 312 mmol) was added over 30 min at 50° C. and the mixture was aged at 50° C. for 15 min. Progress of the reaction is monitored by HPLC analysis: 60:40 Acetonitrile/5.0 mM of each $KH_2PO_4$ and $K_2HPO_4$, 1.0 mL/min. Approximate retention times:

| retention time (min.) | identity |
|---|---|
| 4.1 | hydroxy amide 10 |
| 6.3 | cis-aminoindanol 9 |
| 12.5 | ester amide by product |

After complete acid chloride addition and 15 min. age at 50° C., the HPLC assay of the slurry mixture showed ~0.1 area % of 10. After this point, the reaction mixture was heated to 75° C.

The temperature was increased to 75° C. to dissolve the hydroxyamide 10 in DEM and simplify the phase separations. The aqueous phase was separated and the organic phase was washed twice with water (250 mL). The sodium tartrate was removed in the aqueous phase. The first aqueous cut had a pH of 8.98. The pH of the two water washes were 9.1 and 8.1, respectively. The washed organic phase was concentrated and dried via atmospheric distillation. Approximately 1.0 L of distillate was collected and 750 mL of fresh DEM was charged back to the distillation pot. The atmospheric distillation was continued until another 350 mL of distillate was collected. The solution KF was 93 mg/L. The dried DEM solution was cooled to 30° C. and treated with 63 mL of 2-methoxypropene followed by 0.95 g of MSA. The pH of 1.0 mL sample diluted with 1.0 mL water is 3.2. The reaction mixture was aged at 35°–42° C. for 2 h.

The acetonide formation was monitored by HPLC analysis using the same conditions as described above in this Example. Approximate retention times: same as above. The mixture is aged at 38°–40° C. until 10 is ≦0.7 A%. A typical HPLC area % profile is as follows: 0.4 area % of hydroxy amide, 96.9 area % of acetonide 11, 0.2 area % of ester amide by product, 1.1 area % of methylene ketal impurity. The reaction mixture was cooled to 20° C., filtered to remove the cloudy appearance and quenched with 520 mL of 5% aqueous sodium bicarbonate solution. The aqueous phase was separated and the organic phase was washed with 500 mL of water. The pH of the water wash is 7.4. The washed organic phase (~2.0 L) was concentrated via atmospheric distillation at 78° C. to 80° C. to final volume of 1.0 L. The acetonide concentration in the isolation was maintained at ~525 g/L to minimize isolation losses. The hot DEM solution of 11 was allowed to cool to 50°–52° C., seeded with 100 mg of product and further cooled to 5° C. and aged for 20 min. The batch started to crystallize out of solution at 50° C. The product was isolated by filtration and the wet cake was washed with cold (0° C.) DEM (2×40 mL). The washed cake was dried under vacuum (26" of Hg) at 30° C. to afford 83.8 g of acetonide 11 (87.9 %, >99.5 area % by HPLC).

EXAMPLE 10

| Preparation of Acetonide 11 (Isopropyl Acetate Solvent) | | |
|---|---|---|
| (−)-cis-1-aminoindan-2-ol (9) (98.5 wgt. %) | 80 g | 535 mmol |
| isopropyl acetate (IPAC) | 1.2 L | |
| water | 560 mL | |
| 5N sodium hydroxide | 116 mL | 580 mmol |
| 3-phenylpropionyl chloride (12) | 90.8 g | 539 mmol |
| methanesulfonic acid (MSA) | 1.1 mL | 17.0 mmol |
| 2-methoxypropene (95% by GC) | 119 mL | 1.24 mol |
| 5% aqueous NaHCO$_3$ | 950 mL | |
| water | 400 mL | |
| methyl cyclohexane | 2.25 L | |

A mixture of (−)-cis-1-aminoindan-2-ol 9 (80 g, 535 mmol) in 1.2 L of IPAC and 560 mL of water was treated with 12 (90.8 g, 539 mmol) while the pH was maintained between 8.0–10.5 at 70°–72° C. with 5N sodium hydroxide (116 mL, 580 mmol).

Progress of the reaction was monitored by HPLC analysis: 60:40 Acetonitrile/5.0 mM of each KH$_2$PO$_4$ and K$_2$HPO$_4$. Approximate retention times:

| retention time (min.) | identity |
|---|---|
| 4.1 | hydroxy amide 10 |
| 6.3 | cis-aminoindanol 9 |
| 12.5 | ester amide by product |

At the end of the reaction, the aqueous phase was separated and the organic phase was washed with water (400 mL) at 72° C.–73° C. The pH of the aqueous phase and the aqueous wash was 8.1 and 7.9, respectively. The wet IPAC phase was dried via atmospheric distillation. A total of 3.0 L of IPAc was charged to lower the batch KF to <100 mg/L. The final volume is ~1.60 L. The resulting IPAC slurry of hydroxyamide 10 was treated with 2-methoxypropene (119 mL, 1.24 mol) followed by MSA (1.1 mL, 3.2 mole %) at 35° C.–38° C. for 4.5 h. The acetonide formation was monitored by HPLC analysis using the same conditions as described above. The mixture was aged at 38°–40° C. until 10 is ≦0.4 area %. The reaction was filtered to remove the hazy precipitate and the filtrate was quenched into cold sodium bicarbonate solution (950 mL) over 15 min. The aqueous phase was separated and the organic phase was washed with water (400 mL). The sodium bicarbonate solution was cooled to 0° C.–5° C. The pH of the aqueous phase and the aqueous wash was found to be 7.5 and 7.9, respectively. Atmospheric distillation was carded out while the solvent was switched to methylcyclohexane from IPAC. The initial volume before atmospheric concentration was 1.65 L. A total of 1.5 L of methylcyclohexane was added to complete the solvent switch to methylcyclohexane from IPAC. The batch temperature at the end of the solvent switch was 101 ° C. and the final batch volume was ~900 mL. The batch was heated to 65° C.–70° C. to insure dissolution of the solids, then cooled to 55° C., seeded with the product and cooled to 0° C. The mixture was aged at 0° C. for 15 min and the product was isolated by filtration and washed with cold methylcyclohexane (200 ml). The washed cake was dried under vacuum (26" of Hg) at 30° C. to afford 151 g of acetonide 11 (87.5 %, >99.5 area % by HPLC).

EXAMPLE 11

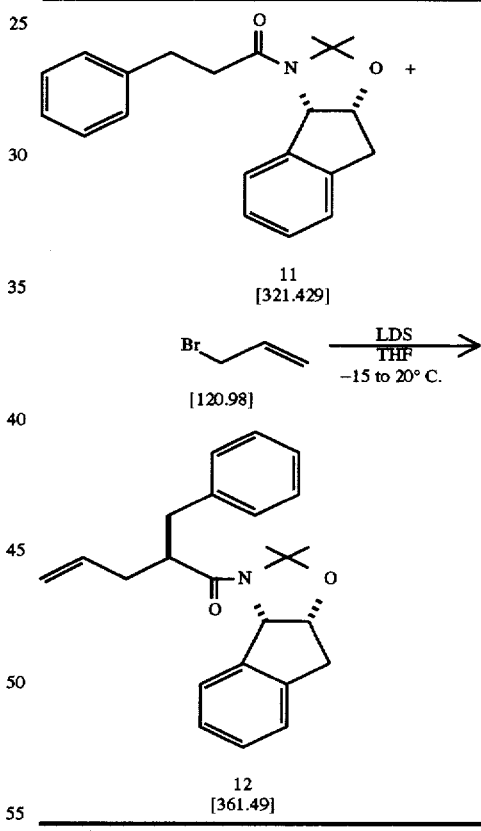

| Acetonide (11) (99.1 wt. %) | [321.42] | 200 g | | 0.617 mol. |
|---|---|---|---|---|
| Allyl Bromide | [120.98] | 77.6 g | 53.6 mL | 0.642 mol |
| LDS (FMC 9404) | 1.32M in THF | | 518 mL | 0.684 mol |
| Citric acid | [192.1] | 35.73. g | | 0.186 mol |
| THF sieve dried, | | 1.43 L | | |
| Water | | 1.05 L | | |
| 0.3M H$_2$SO$_4$ | | 1.18 L | | |
| 6% NaHCO$_3$ | | 1.18 L | | |
| IPAc | | | | |

The crystalline acetonide 11 (200 g, 0.622 mol, 99.1 wt. %) was dissolved in 1.25 L sieve dried THF (KF=11 mg/L)

under nitrogen atmosphere at 25° C. with mechanical stirring. The resulting KF of the solution at this point was 40 mg/L. The solution was subjected to three alternating vacuum/nitrogen purge cycles to thoroughly degas the solution of dissolved oxygen.

Allyl bromide was added to the THF solution. The resulting KF was 75 mg/L. Typical complete conversion (>99.5%) has been obtained with pre-LDS solution KF levels of 200 mg/L with the 10% base excess present in this procedure. The solution was then cooled to −20° C. A THF solution of lithium hexamethyldisilazide (LDS. 1.32M) was added to the allyl bromide/11 solution at such a rate as to maintain the reaction temperature at −20° C. The LDS addition took 30 min. The mixture was aged at −15 to −20° C. and quenched when the conversion was >99%. Analysis of the reaction was carried out by HPLC. Approximate retention times: hydroxyacetonide by product=5.3 min, ethyl benzene=5.6 min, acetonide 11=6.6 min; allyl acetonide 12=11.8 min; epi-12=13.3 min. After 1 h, the reaction had gone to >99.5% conversion. The reaction was quenched by the addition of a solution of citric acid (35.7 g, 0.186 mol) in 186 mL of THF. The mixture was aged at 15° C. for 30 min following the citric acid addition. The mixture was concentrated at reduced pressure (about 28" Hg) to about 30% of the initial volume while maintaining a pot temperature of 11°–15° C. and collecting 900 mL of distillate in a dry ice-cooled trap. The solvent was then switched using a total of 2.7 L of isopropyl acetate (IPAc) while continuing the reduced pressure distillation. The solvent switch was stopped when <1 mole % THF remained by $^1$H NMR (see analytical report for GC method). The maximum temperature during the distillation should not exceed 35° C. The crude mixture in IPAc was washed with 1.05 L of distilled water, 1.18 L of 0.3M sulfuric acid, and 1.18 L of 6% aqueous sodium bicarbonate. The volume of the organic phase after the washes was 1.86 L.

The pH of the mixture after the three aqueous washes was 6.5, 1.3 and 8.5, respectively. HPLC analysis of the mixture at this point indicated 93–94% assay yield for 12. The ratio of the desired 12:epi-12 was 96:4 by HPLC (same conditions as above). GC analysis at this point indicated that the hexamethyldisilazane by-product had been completely removed in the workup.

EXAMPLE 12

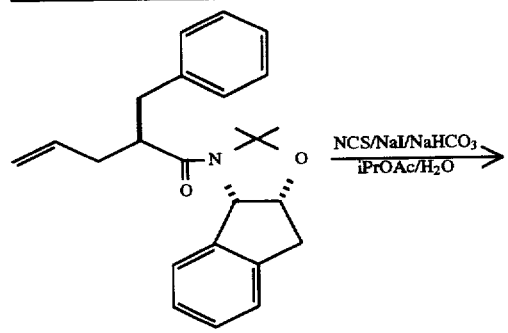

12
[361.49]

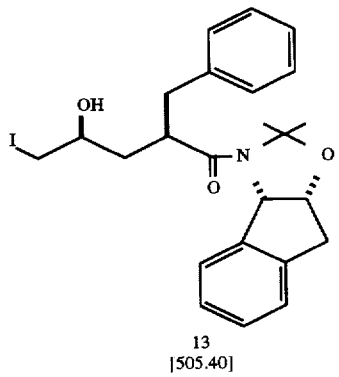

13
[505.40]

| | | | |
|---|---|---|---|
| NCS | [133.5] | 141.2 g | 1.06 mol |
| NaHCO$_3$ | [84.01] | 36.6 g | 0.434 mol |
| NaI | [149.9] | 158.6 g | 1.06 mol |
| Na$_2$SO$_3$ | [126.0] | 80 g | |
| Water | | 1.55 L | |

To the allyl amide 12 solution in IPAc from the previous step at 25° C. was added a solution of 36.6 g of sodium bicarbonate in 1.03 L of distilled water and the biphasic mixture was cooled to 5° C. Solid N-chlorosuccinimide (141.2 g, 1.06 mol) was added. There was no exotherm after the addition of NCS. To this mixture was added an aqueous solution of sodium iodide (158.6 g, 1.06 mol) while maintaining the reaction mixture at 6°–11° C. The addition took 30 min, and the mixture became dark. The mixture was warmed to 25° C. and aged with vigorous stirring. Progress of the reaction was monitored by HPLC: same system as above, approximate retention times: iodohydrins 13, epi-13, bis-epi-13=8.1 min; allyl amide 12=11.8 min. Analysis of the mixture by HPLC after 2.25 h indicated >99.5% conversion. The approximate diastereomer ratio of 13:epi-13:bis-epi-13 in the crude mixture is roughly 94:2:4 at this point when resolution of the components can be obtained on this system. The agitation was discontinued and the layers were separated. To the organic phase was added aqueous sodium sulfite (80 g, 0.635 mol in 400 mL) over 10–15 min. The temperature of the mixture rose from 26°–29° C. after the sodium sulfite addition. The mixture was agitated for 40 min at 25° C. The solution was substantially decolorized after the sulfite wash. The layers were separated; the KF of the organic phase at this point was 25 g/L. The volume of the organic phase was 1.97 L. Quantitative analysis of the mixture by HPLC (same system as above) indicated a 86% overall assay yield of the iodohydrin 13 at this point (corrected for coeluting diastereomers).

EXAMPLE 13

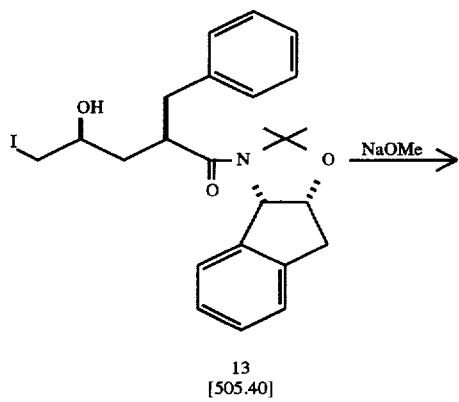

13
[505.40]

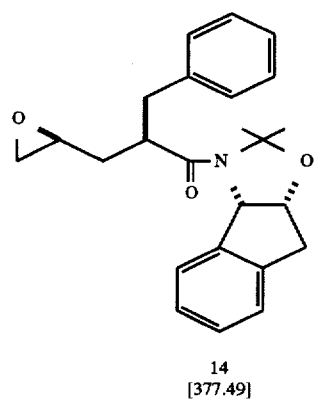

14
[377.49]

| | | | | |
|---|---|---|---|---|
| NaOMe<br>0.796 mol | [54.02] | d = 0.945 | 25 wt % in MeOH | 172 g |
| 3% aqueous Na$_2$SO$_4$ | | | | 1.5 L |
| n-PrOH | | | | |

The solution of the iodohydrin 13 was concentrated in vacuo (28" Hg) to azeotropically dry the batch. A total of 700 mL of distillate was collected while maintaining a batch temperature of 22°–28° C. The distillate was replaced with 500 mL of IPAc (KF=275 mg/L).

The solution was cooled to 26° C. and 25% NaOMe/MeOH solution (168.1 g) was added over a 10 min period. The temperature dropped to 24° C. after the addition of sodium methoxide. The mixture became darker and a gummy solid briefly formed which redissolved. The mixture was aged for 1 h at 25° C. Analysis of the reaction was carded out by HPLC (same conditions as above), approximate retention times: epoxide epi-14=6.5 min, epoxide 14, bis-epi-14=7.1 min, iodohydrin 13=8.1 min. HPLC analysis indicated 99% conversion of the iodohydrin to the epoxide. After an additional 40 min, 4.1 g of the sodium methoxide/methanol solution was added. After 20 min, HPLC analysis indicated 99.5% conversion. The reaction was quenched by the addition of 366 mL of water at 25° C. which was then agitated briefly (10 min) and the layers were separated. It was subsequently found that extended aging of the reaction and water wash agitation/settling gave substantial back reaction to iodohydrin under these conditions in the pilot plant. This problem is especially acute in the water washes. To eliminate this problem, the reaction was run at 15° C. After >99% conversion was achieved (1 h after NaOMe addition), the mixture was diluted with IPAc (40% of batch volume) and initially washed with an increased volume of water (732 mL) at 20° C. Colder temperatures and more concentrated mixtures can result in the premature precipitation of 14 during the washes. The agitation/settling times were kept to a minimum (10 min/30 min, respectively). In this way, the back reaction could be limited to ≦1%. Crude mixtures containing (97:3) epoxide 14/iodohydrin 13 have been carried forward in the isolation to afford epoxide product containing 0.6% iodohydrin. Epoxide product containing this level of iodohydrin has been carded forward without complication. The organic phase was washed with 3% aqueous sodium sulfate (2×750 mL). The volume of the organic phase was 1.98 L after the washes. The pH of the three water washes was 10.7, 9.4 and 8.6, respectively. HPLC analysis indicated a 86% overall assay yield of epoxide 14 at this point (corrected for 4% co-eluting bis-epi-14). The IPAc solution of epoxide 14 was concentrated at reduced pressure (28" Hg) to a volume of about 600 mL while maintaining the batch at 15°–22° C. The solvent was switched to n-PrOH by adding 750 mL n-PrOH while vacuum concentrating to a pot volume of about 500 mL, maintaining the batch at <30° C. Temperatures >35° C. during the concentration/solvent switch can give an n-propyl ether as a degradation by-product derived from epoxide 14. Analysis of the solvent composition by $^1$H NMR showed <1 mol % IPAc remaining. The thick slurry was cooled to –10° C. over an hour and aged for 45 min. The solids were filtered and washed with 125 mL of cold nPrOH. The product was dried in a vacuum oven at 25° C. to afford 188.5 g of epoxide 14 (98.9 A %, 97.6 wt. %, 0.8 wt. % epi-14, 79.3% yield overall from 11.) Normal phase HPLC (see analytical research memo for procedure) indicated no bis-epi-14 present in the isolated solids.

EXAMPLE 14

Preparation of Penultimate 16

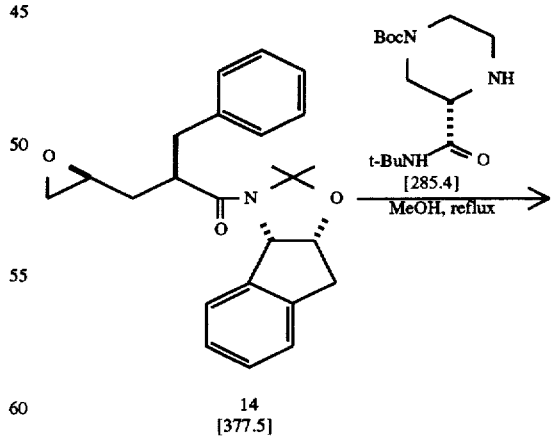

14
[377.5]

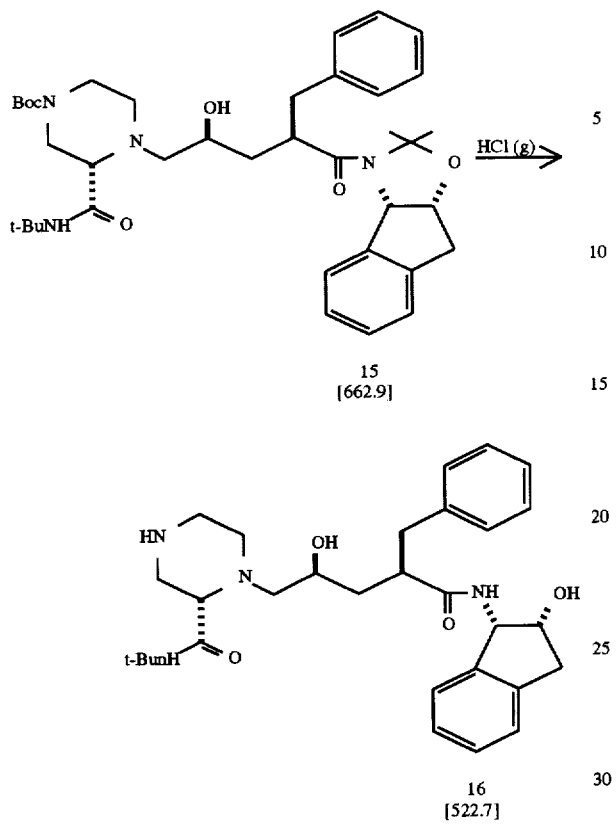

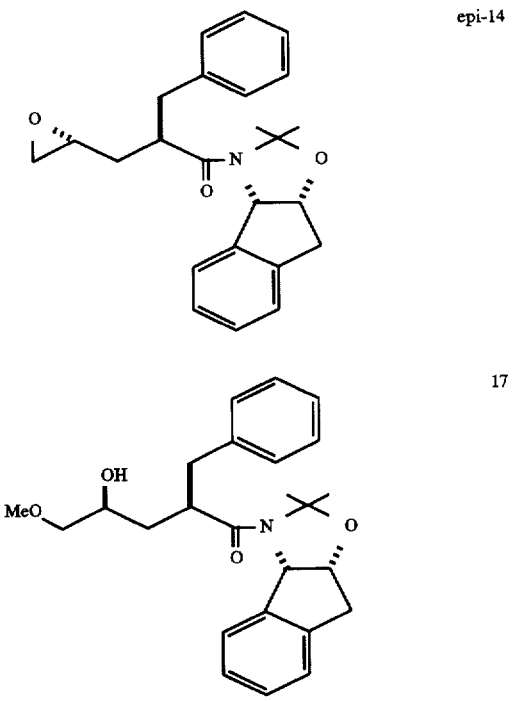

| 2(S)-t-butylcarboxamide-4-N-Boc-piperazine 3 (98.9 wt. %, 99.6% ee) | 159 g | 557 mmol |
|---|---|---|
| epoxide 14 (97.6 wt. %, 1.0% epi-14) | 200 g | 530 mmol |
| methanol | 1.06 L | |
| HCl(g) | 194 g | 5.32 mol |
| 23% NaOH | 740 mL | |
| isopropyl acetate | 4.0 L | |
| water | 700 mL | |

*corrected for wt. % purity

Solid 2(S)-t-butylcarboxamide-4-t-butoxycarbonyl-piperazine 3 (159 g, 557 mmol) and the epoxide 14 (200 g, 530 mol) were added to a 2 L three neck flask, equipped with a mechanical stirrer, reflux condenser, heating mantle, teflon coated thermocouple and nitrogen inlet. Methanol (756 mL) was added and the resulting slurry was heated to reflux temperature. After 40 min, a homogeneous solution was obtained. The internal temperature during reflux was 64°–65° C. Progress of the reaction was monitored by HPLC analysis: 60:40 acetonitrile/10 mM ($KH_2PO_4/K_2HPO_4$). Approximate retention times:

| retention time (min) | identity |
|---|---|
| 4.8 | piperazine 3 |
| 6.6 | methyl ether 17 |
| 8.2 | epoxide epi-14 |
| 8.9 | epoxide 14 |
| 15.2 | coupled product 15 |

The mixture was maintained at reflux until epoxide 14 was between 1.2 to 1.5 area % by HPLC analysis. The coupled product at this point was about 94–95 area %. The methyl ether 17 was present at 1.0–1.5 A% at completion. Typical time to achieve this conversion was 24–26 h at reflux.

The mixture was cooled to −5° C. and anhydrous HCl gas (194 g, 5.32 moles, ~10 equiv.) was bubbled directly into the methanol solution under nitrogen atmosphere while keeping the temperature between 5°–8° C. over 2–3 h. After the addition was complete, the mixture was aged between 5°–8° C. for 1–3 h. Evolution of gas was observed at this point (carbon dioxide and isobutylene). Progress of the reaction was monitored by HPLC analysis: same conditions as above. Approximate retention times:

| retention time (min) | identity |
|---|---|
| 6.0 | Boc intermediate 18 |
| 7.0 | cis-aminoindanol 19 |
| 11.9 | penultimate 16 |
| 15.1 | coupled product 15 |
| 16.5 | lactone 20 |
| 25.0 | acetonide intermediate 21 |

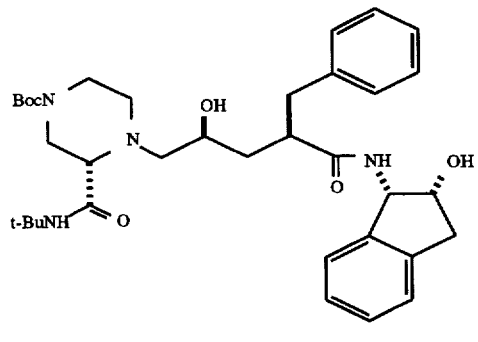

-continued

| retention time (min) | identity |
|---|---|

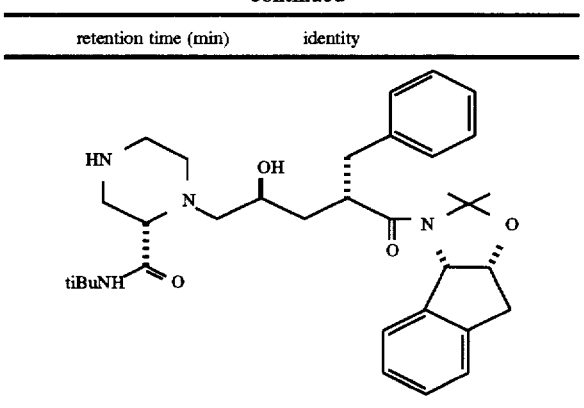

21

The mixture was aged at 5° to 8° C. until Boc intermediate 18 is <0.5 area % by HPLC analysis. At this point, penultimate 16 was about 92–93 A %, 19 was <1.0 A% and 20 was 0.6 A % by HPLC analysis. The deblocking was complete after 4 h at 5° C. Cooling and quenching the reaction promptly upon completion limits decomposition of 16 to 19 and 20 under the hydrolysis conditions.

19

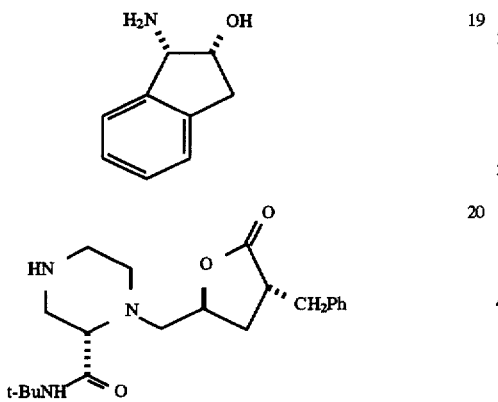

20

The mixture was cooled to −10° to −15° C. This mixture was then slowly added to a 5 liter flask equipped with a mechanical stirrer containing a cold, stirred solution of DI water (700 mL) and methanol (300 mL) at 0°–2° C.; the pH of the quenched mixture was maintained between 8.5–9.0 by addition of 23 wgt. % aqueous NaOH solution (giving a highly exothermic reaction) while keeping the temperature between 10°–20° C. The final batch pH was 9.0–9.5.

The mixture was extracted with isopropyl acetate (3.0 L). The mixture was agitated and the layers were separated. The spent aqueous phase was re-extracted with isopropyl acetate (1.0 L). HPLC assay yield of 16 in isopropyl acetate at this point is 94%.

The combined organic phase (~5.0 L) was concentrated under reduced pressure (24–25" of Hg) to a volume of about 1.12 L at a batch temperature of 30°–40° C. The pot temperature during the solvent switch can rise to 40° C. with no penalty in yield or degradation. This solution of crude 16 was then used directly in the next step to afford compound J.

EXAMPLE 15

Preparation of monohydrate

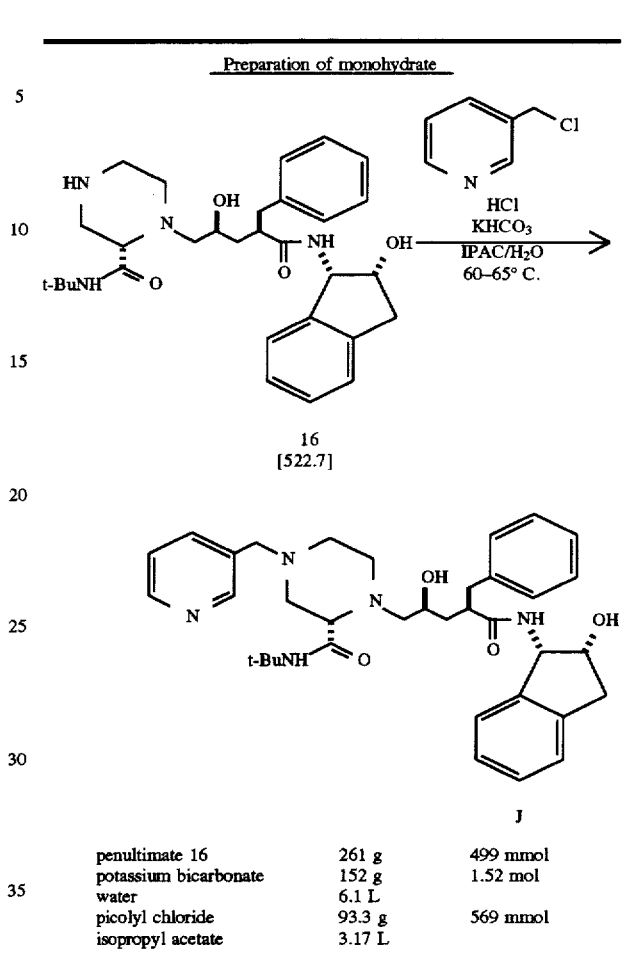

| penultimate 16 | 261 g | 499 mmol |
|---|---|---|
| potassium bicarbonate | 152 g | 1.52 mol |
| water | 6.1 L | |
| picolyl chloride | 93.3 g | 569 mmol |
| isopropyl acetate | 3.17 L | |

An isopropyl acetate solution of penultimate (4.96 L; 52.5 g/L of penultimate) was concentrated under reduced pressure to a volume of 1.18 L (260 g, 499 mmol). The batch temperature was maintained between 35° C. to 44° C. while keeping vacuum pressure at 25" of Hg. The methanol content was less than <1.0 vol %.

The resulting slurry was treated with an aqueous solution of potassium bicarbonate (152 g in 630 mL of water, 1.59 mol, ~3.0 equiv.) and heated to 60° C. Then, an aqueous solution of picolyl chloride (93.8 g in 94 mL of water; 572 mmol, 1.14 equiv.) was added over 4 hours. The batch was seeded with compound J monohydrate after charging 75% of the picolyl chloride charge. The batch temperature was between 60° C. to 65° C.

At the end of the addition, the slurry mixture was aged for 20 h between 60° C. to 65° C. The reaction was complete when the penultimate is <1.0 area % by HPLC analysis. The picolyl chloride level was between 0.5 to 0.8 area %.

The batch was then diluted with 2.5 L of isopropyl acetate and 1.34 L of water and heated to 78° C. The layers were separated and the organic phase was washed with hot water (3×1.34 L) at 78° C. The hot water wash removed the bis-alkylated compound J and the level was reduced to <0.1 area % by HPLC analysis.

The organic phase was slowly cooled to 75° C. and seeded with compound J monohydrate (8.0 g) and then further cooled to 4° C. over 2 h. The mixture was filtered to collect the product and the wet cake was washed with cold isopropyl acetate (2×335 mL). The wet cake was dried in vacuo (28" Hg, 22° C.) to afford 273 g of compound J monohydrate in 79% isolated yield from the epoxide.

EXAMPLE 16

Pyrazine-2-tert-butyl carboxamide 23

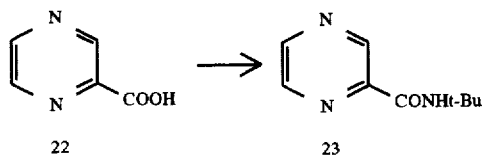

| | |
|---|---|
| 2-Pyrazinecarboxylic acid (22) | 3.35 kg (27 mol) |
| Oxalyl chloride | 3.46 kg (27.2 mol) |
| tert-Butylamine (KF = 460 μg/ml) | 9.36 L (89 mol) |
| EtOAc (KF = 56 μg/ml) | 27 L |
| DMF | 120 mL |
| 1-Propanol | 30 L |

The carboxylic acid 22 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5° and 8° C.

The addition was completed in 5 h. During the exothermic addition CO and $CO_2$ were evolved. The HCl that was formed remained largely in solution. A precipitate was present which is probably the HCl salt of the pyrazine acid chloride. Assay of the acid chloride formation was carded out by quenching an anhydrous sample of the reaction with t-butylamine. At completion <0.7% of acid 22 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 22=10.7 min, amide 23=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 23 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The internal temperature in this solvent change was <30° C. A 1-propanol/EtOAC solution of 3 was stable to reflux atatmospheric pressure for several days.

Evaporation of an aliquot gave a tan solid m.p 87°–88° C. $^{13}C$ NMR (75 MHz, $CDCl_3$, ppm) 161.8, 146.8, 145.0, 143.8, 142.1, 51.0, 28.5.

Materials

Pyrazine-2-tert-butylcarboxamide 23 2.4 kg (13.4 mol) in 1-Propanol solution 12 L 20% $Pd(OH)_2/C$ 16 wt.% water 144 g.

The, pyrazine-2-tert-butylcarboxamide 23/1 -propanol solution was placed into the 5 gal autoclave. The catalyst was added and the mixture was hydrogenated at 65° C. at 40 psi (3 atm) of $H_2$.

After 24 h the reaction had taken up the theoretical amount of hydrogen and GC indicated <1% of 23. The mixture was cooled, purged with $N_2$ and the catalyst was removed by filtration through Solka Floc. The catalyst was washed with 2 L of warm 1 -propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 23=7.0 min, 24=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 24 is 133 g/L.

Evaporation of an aliquot gave 24 as a white solid m.p. 150°–151° C.; $^{13}C$ NMR (75 MHz, $D_2O$, ppm) 173.5, 59.8, 52.0, 48.7, 45.0, 44.8, 28.7.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A chiral hydrogenation process for the synthesis of a chiral piperazine, of the structure

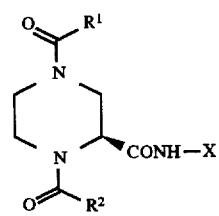

wherein $R^1$ and $R^2$ are independently OX, and X is $C_{1-4}$ alkyl unsubstituted or substituted with aryl or trihalo, comprising the steps of:

(a) providing a quantity of the compound

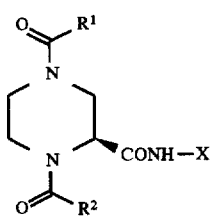

(b) mixing thereto between about 0.1 mole % and about 5 mole % of the catalyst of the structure:
  (diene) Rhodium (chiral bisphosphine) (anionic counterion); or
  (diene) Iridium (chiral bisphosphine) (anionic counterion);
wherein the anionic counterion is selected from the group consisting of perchlorate, tetrafluoroborate, triflate, hexafluorophosphate, and hexafluoroantimonate anion;
  (c) hydrogenating the mixture in solvent in the presence of a hydrogen source, at a temperature between about −10° C. and about 150° C.;
  (d) to give the desired chiral piperazine.

2. A chiral hydrogenation process for the synthesis of a chiral piperazine, of the structure

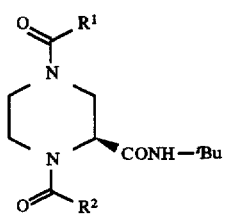

wherein $R^1$ and $R^2$ are independently OX, and X is $C_{1-4}$ alkyl unsubstituted or substituted with aryl or trihalo, comprising the steps of:
(a) providing a quantity of the compound

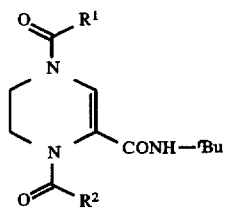

(b) mixing thereto between about 0.1 mole % and about 5 mole % of the catalyst of the structure:
  (diene) Rhodium (chiral bisphosphine) (anionic counterion); or
  (diene) Iridium (chiral bisphosphine) (anionic counterion);
wherein the anionic counterion is selected from the group consisting of perchlorate, tetrafluoroborate, triflate, hexafluorophosphate, and hexafluoroantimonate anion;
  (c) hydrogenating the mixture in solvent in the presence of a hydrogen source, at a temperature between about −10° C. and about 150° C.;
  (d) to give the desired chiral piperazine.

3. The process of claim 1 or 2, wherein
  $R^1$ is OtBu;
  $R^2$ is OBn.

4. The process of claim 1 or 2, wherein the diene of the catalyst is selected from the group consisting of 1,5-cyclooctadiene, bicyclo[2.2.1]hepta-2,5-diene, 1,5-hexadiene and two ethylene molecules.

5. The process of claim 1 or 2, wherein the chiral bisphosphine is selected from the group consisting of

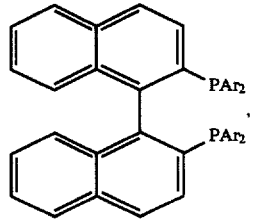

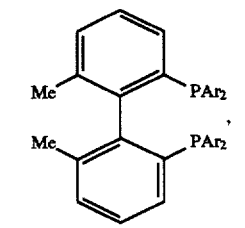

or

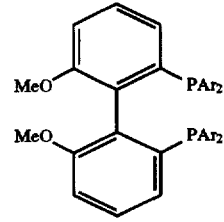

wherein Ar is Ph or tolyl.

6. The process of claim 1 or 2 wherein the solvent contains alcohol, said alcohol selected from the group consisting of trifluoro ethanol, methanol, ethanol, n-propyl alcohol, isopropyl alcohol, amyl alcohol, butanol, and pentanol.

7. The process of claim 1 or 2 wherein the source of hydrogen of Step c) is selected from the group consisting of hydrogen gas, ammonium formate, hydrazine or triethylammonium formate.

8. The process of claim 7, wherein the source of hydrogen is hydrogen gas, and Step c) is carried out under a pressure of between about 0.3 and about 300 atmospheres.

9. The process of claim 8, wherein the pressure is between about 2 and about 300 atmospheres.

10. The process of claim 1 or 2, wherein the temperature range of Step c) is between about 20° C. and about 100° C.

11. A chiral hydrogenation process for the synthesis of the chiral piperazine, of the structure

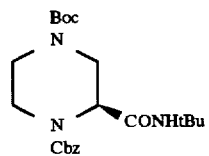

comprising the steps of:

(a) providing a quantity of the compound

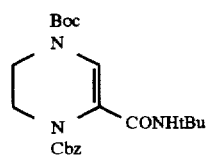

(b) mixing thereto between about 0.1 mole % and about 5 mole % of the catalyst of the structure: (R)—BINAP—Rh—(1,5-cyclooctadiene) triflate;

(c) hydrogenating the mixture in alcoholic solvent under hydrogen at a pressure between about 2 and about 300 atmospheres, at a temperature of between about −10° C. and about 150° C.;

(d) to give the desired chiral piperazine.

* * * * *

UNITED STATES PATENT AND TRADEMARK OFFICE
CERTIFICATE OF CORRECTION

PATENT NO. : 5,723,615  
DATED : March 13, 1998  
INVENTOR(S) : Kai Rossen, Steven A. Weissman, Jess Sager, David Askin, Paul J. Reider, Ralph P. Volante It is certified that error appears in the above-identified patent and that said Letters Patent is hereby corrected as shown below:

At column 5, line 5, delete " 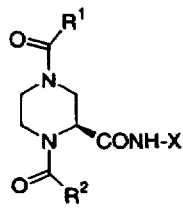 " and insert therefor -- 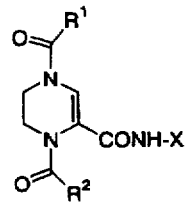 --.

At column 5, line 45, delete " 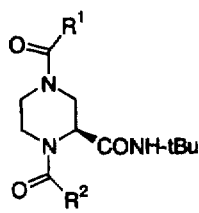 " and insert therefor -- 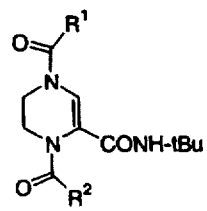 --.

At column 7, line 5, delete "  " and insert therefor -- 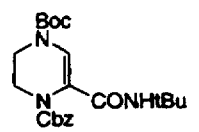 --.

UNITED STATES PATENT AND TRADEMARK OFFICE
CERTIFICATE OF CORRECTION

PATENT NO. : 5,723,615
DATED : March 13, 1998
INVENTOR(S) : Kai Rossen, Steven A. Weissman, Jess Sager, David Askin, Paul J. Reider, Ralph P. Volante It is certified that error appears in the above-identified patent and that said Letters Patent is hereby corrected as shown below:

In the reaction at column 13, line 15, delete " 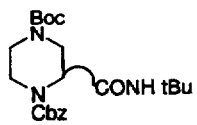 " and insert therefor -- 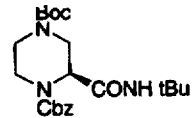 --.

In claim 1, column 33, line 5, delete " 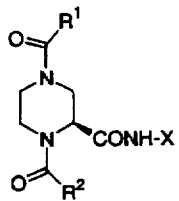 " and insert therefor -- 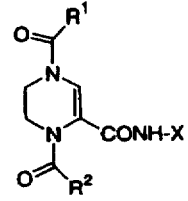 --.

Signed and Sealed this

Thirtieth Day of October, 2001

Attest:

NICHOLAS P. GODICI
Attesting Officer   Acting Director of the United States Patent and Trademark Office